United States Patent
Björklund et al.

(10) Patent No.: US 11,541,082 B2
(45) Date of Patent: Jan. 3, 2023

(54) MICROBIAL COMPOSITIONS

(71) Applicant: Probi AB, Lund (SE)

(72) Inventors: Malin Björklund, Hjärup (SE); Jenny Rudolfsson, Lund (SE)

(73) Assignee: Probi AB, Lund (SE)

( * ) Notice: Subject to any disclaimer, the term of this patent is extended or adjusted under 35 U.S.C. 154(b) by 64 days.

(21) Appl. No.: 16/619,503

(22) PCT Filed: Jun. 5, 2018

(86) PCT No.: PCT/EP2018/064796
§ 371 (c)(1),
(2) Date: Dec. 5, 2019

(87) PCT Pub. No.: WO2018/224509
PCT Pub. Date: Dec. 13, 2018

(65) Prior Publication Data
US 2020/0155619 A1    May 21, 2020

(30) Foreign Application Priority Data
Jun. 5, 2017   (GB) ..................... 1708932

(51) Int. Cl.
| | | |
|---|---|---|
| A61K 35/745 | (2015.01) | |
| A61K 9/14 | (2006.01) | |
| A61K 35/747 | (2015.01) | |
| A61K 47/02 | (2006.01) | |
| A61K 47/26 | (2006.01) | |
| A61K 47/36 | (2006.01) | |

(52) U.S. Cl.
CPC ............. *A61K 35/745* (2013.01); *A61K 9/14* (2013.01); *A61K 35/747* (2013.01); *A61K 47/02* (2013.01); *A61K 47/26* (2013.01); *A61K 47/36* (2013.01)

(58) Field of Classification Search
CPC ...... A61K 35/745; A61K 35/747; A61K 9/14; A61K 47/02; A61K 47/26; A61K 47/36
See application file for complete search history.

(56) References Cited

U.S. PATENT DOCUMENTS

| | | | | |
|---|---|---|---|---|
| 8,846,027 | B2 * | 9/2014 | Kiss ...................... | A61K 35/747 424/93.1 |
| 10,368,569 | B2 * | 8/2019 | Toksoz ...................... | A23L 2/60 |
| 10,835,485 | B2 * | 11/2020 | Pompejus ............... | A61K 35/74 |
| 2005/0013923 | A1 * | 1/2005 | Shimek .................... | A23G 3/52 426/660 |
| 2009/0196921 | A1 | 8/2009 | Ebel et al. | |
| 2011/0027236 | A1 * | 2/2011 | Bastianelli .............. | A61P 19/08 424/93.7 |
| 2012/0058095 | A1 * | 3/2012 | Strozzi ................. | A61K 35/744 424/93.44 |
| 2012/0135017 | A1 | 5/2012 | Harel et al. | |
| 2014/0017337 | A1 * | 1/2014 | Amoruso ............. | A61K 31/198 424/643 |
| 2014/0105864 | A1 * | 4/2014 | Di Leo ................... | A61K 47/42 424/93.4 |
| 2017/0000892 | A1 * | 1/2017 | Harel ..................... | A23K 10/18 |
| 2017/0106029 | A1 * | 4/2017 | Ranganathan ........ | A61K 35/742 |
| 2017/0273895 | A1 * | 9/2017 | Pompejus ............. | A23L 33/135 |
| 2020/0155619 | A1 * | 5/2020 | Bjorklund .............. | A61K 47/36 |
| 2021/0000878 | A1 * | 1/2021 | Chancellor ............ | A61K 35/34 |
| 2021/0100854 | A1 * | 4/2021 | Goodman ............. | A23L 33/195 |
| 2021/0128649 | A1 * | 5/2021 | Ning .................... | A61K 35/747 |

FOREIGN PATENT DOCUMENTS

| | | | | |
|---|---|---|---|---|
| CN | 102204679 | A | 10/2011 | |
| CN | 104328076 | A | 2/2015 | |
| CN | 105685970 | A | 6/2016 | |
| CN | 106666738 | * | 5/2017 | ............. A61K 45/06 |
| EP | 2228067 | A1 | 9/2010 | |
| EP | 2991649 | A1 | 3/2016 | |
| WO | WO-2009103788 | A1 * | 8/2009 | ............. A61K 45/06 |
| WO | WO-2010023248 | A1 * | 3/2010 | ........... A23L 33/135 |
| WO | WO-2010103374 | A2 * | 9/2010 | ............... A61P 1/06 |
| WO | 2010/114864 | A1 | 10/2010 | |
| WO | 2013/001089 | A1 | 1/2013 | |
| WO | WO-2013001089 | A1 * | 1/2013 | ........... A23C 9/1526 |
| WO | WO-2014076638 | A1 * | 5/2014 | ........... A61K 31/426 |
| WO | 2014/176632 | A1 | 11/2014 | |
| WO | 2015/153841 | A1 | 10/2015 | |
| WO | 2017/019273 | A1 | 2/2017 | |

(Continued)

OTHER PUBLICATIONS

Hulthen et al, American Journal of Hematology, Mar. 2016, 91/3:E144. Abstract No. 121 abstract only (Year: 2016).*
Bjorklund et al., AGE 2012, 34:987-999. Published online: Aug. 19, 2011. (Year: 2011).*
Bjorklund, Additional trials for Fast Melt Technology (PRO 35-P-PCT). Annex 1, Report Fast Melt Patent—Additional trials. Probi, www.probi.com. 4 pages, May 27, 2020.
Mintel, Dietary Supplement. Retrieved online at: http://www.gnpd.com, 4 pages, (2017).
Mintel, Priobiotics Supplement. Retrieved online at: http://www.gnpd.com, 4 pages, (2015).
International Search Report and Written Opinion for Application No. PCT/EP2018/064796, dated Sep. 26, 2018, 10 pages.
Adhikari et al., Stickiness in Foods: A Review of Mechanisms and Test Methods. Int J Food Properties 2001;4(1):1-33.

(Continued)

*Primary Examiner* — Gary B Nickol
*Assistant Examiner* — Amelia Nicole Dickens
(74) *Attorney, Agent, or Firm* — McCarter & English, LLP; Yu Lu

(57) ABSTRACT

The invention provides a microbial composition in the form of a powder for oral administration comprising or consisting of: (i) micro-organism, preferably probiotic bacteria; (ii) sugar alcohol, such as Erythritol and Xylitol; (iii) moisture absorbent fibre, such as inulin; (iv) a flow agent, such a silicon dioxide optionally; (v) a flavorant; and/or optionally (vi) a bulking agent, such as maltodextrin. The compositions display good storage stability, fast-melt and sensory properties. They are preferably packaged in a single dose in a sealed stick pack aluminium container.

12 Claims, 7 Drawing Sheets

(56) References Cited

FOREIGN PATENT DOCUMENTS

WO 2017/060477 A1 4/2017
WO WO-2018224509 A1 * 12/2018 ........... A61K 35/745

OTHER PUBLICATIONS

Beneo, Orafti Inulin from Natural Sources Retrieved online at: https://www.beneo.com/Ingredients/Human-Nutrition/Functional-Fibres/Inulin/, 2 pages, (2013).
Drugs.com, Silicon Dioxide. Retrieved online at: https://www.drugs.com/inactive/silicon-dioxide-170.html, 1 page, (2017).
Grace, Pharmaceutical Excipients. Retrieved online at: https://grace.com/pharma-and-biotech/en-US/excipients-and-drug-delivery, 2 pages, (2017).
Grace, Syloid Silicas Pharmaceutical Excipients Technical Note. Retrieved online at: https://grace.com/, 3 pages, (2015).
Mintel, 20+10 Microcapsules Probiotic Powder for Kids. Retrieved online at: http://www.gnpd.com, 3 pages, (2012).
Mintel, Dietary Supplement with Probiotics. Retrieved online at: http://www.gnpd.com, 3 pages, (2012).
Mintel, Probiotics for Kids. Retrieved online at: http://www.gnpd.com, 3 pages, (2012).
Mintel, Tropical Water Mix. Retrieved online at: http://www.gnpd.com, 3 pages, (2012).
Probi AB, Press Release. Probi launches a tasty and convenient way of taking your daily probiotic supplement. 1 page. Sep. 22, 2017.
Prospector, Orafti ST-Gel. Retrieved online at: https://www.ulprospector.com/en/na/Food/Detail/3982/356776/Orafti-ST-Gel. 2 pages. 2017.
Prospector, Syloid 244 FP. Retrieved online at: https://www.ulprospector.com/en/eu/Food/Detail/985/107455/SYLOID-244-FP. 2 pages. 2017.
Tereos, Maltodextrin. Retrieved online at: http://www.tereos-starchsweeteners.com. 2 pages. 2017.
University of Florida Center for Smell and Taste, Taste vs. Flavor: What's the Difference? Retrieved online at: http://cst.ufl.edu/taste-vs-flavor-whats-the-difference.html, 3 pages, (2015).
Wikipedia, Erythritol. Retrieved online at: https://en.wikipedia.org/wiki/Erythritol. 4 pages. 2017.
Wikipedia, Inulin. Retrieved online at: https://en.wikipedia.org/wiki/Inulin. 5 pages. 2017.
Wikipedia, Xylitol. Retrieved online at: https://en.wikipedia.org/wiki/Xylitol. 8 pages. 2017.

* cited by examiner

Viable count, CFU/dose (1 g)

Water activity

|  | 0 | 1 | 2 | 3 | 6 | 9 | 12 | Months |
|---|---|---|---|---|---|---|---|---|
| Fast Melt formulation (Lp299v) | 0,09 | 0,10 | 0,12 | 0,16 | 0,12 | 0,10 | 0,12 | |

Viable count, CFU/dose (1 g)

Water activity

|  | 0 | 1 | 2 | 3 | 6 | 9 | 12 | 18 | Months |
|---|---|---|---|---|---|---|---|---|---|
| Fast Melt Lp299v | 0,09 | 0,10 | 0,12 | 0,16 | 0,12 | 0,10 | 0,12 | 0,13 | |

Viable count, CFU/dose (1 g)

Water activity

|  | 0 | 1 | 2 | 3 | Months |
|---|---|---|---|---|---|
| Fast Melt formulation (Lp299v) | 0,11 | 0,13 | 0,16 | 0,13 | |

Viable count, CFU/dose (1 g)

Water activity

|  | 0 | 1 | 3 | 6 | 9 | 12 | 18 | Months |
|---|---|---|---|---|---|---|---|---|
| Fast Melt Lpa13434 / Lp15312 | 0,10 | 0,19 | 0,17 | not tested | not tested | 0,16 |  |  |

Viable count, CFU/dose (1 g)

Water activity

|  | 0 | 1 | 3 | 6 | 9 | 12 | 18 | Months |
|---|---|---|---|---|---|---|---|---|
| Fast Melt Lpa13434 | 0,10 | not tested | not tested | not tested | not tested | 0,16 | | |

Viable count, CFU/dose (1 g)

Water activity

|  | 0 | 1 | 3 | 6 | 9 | 12 | 18 | Months |
|---|---|---|---|---|---|---|---|---|
| Fast Melt Lp6595 | 0,11 | 0,21 | 0,20 | not tested |  |  |  |  |

Viable count, CFU/dose (1 g)

Water activity

|  | 0 | 1 | 3 | 6 | 9 | 12 | 18 | Months |
|---|---|---|---|---|---|---|---|---|
| Fast Melt Lrh6594 | 0,13 | 0,23 | 0,21 | not tested | | | | |

MICROBIAL COMPOSITIONS

CROSS-REFERENCE TO RELATED APPLICATIONS

This application is a U.S. national stage filing, under 35 U.S.C. § 371(c), of International Application No. PCT/EP2018/064796, filed on Jun. 5, 2018, which claims priority to United Kingdom Patent Application No. 1708932.7, filed on Jun. 5, 2017. The entire contents of each of the aforementioned applications are incorporated herein by reference.

The present invention relates to a microbial composition and preferably a probiotic composition for oral administration to a subject, preferably a human. In particular, the invention relates to a fast-melt microbial composition in the form of a powder.

The invention also relates to methods for making and using the compositions and to packaged compositions, especially compositions packaged for oral administration to a subject in one or more predetermined doses.

BACKGROUND TO THE INVENTION

It is known to provide a variety of different microbial, that is, micro-organism-containing compositions. A particular technical problem with such compositions is how to maintain the viability of sufficient numbers of the micro-organisms during storage, so that upon administration to a subject there are sufficient viable micro-organisms to confer the desired probiotic effect.

WO 2017/060477 A1 (BIFODAN NS) relates to a nutritional composition comprising probiotic bacteria formulated as a fast melting composition comprising a low calorie sweetener, a hygroscopic agent and an aroma compound. It is disclosed that magnesium oxide; silicon dioxide; and calcium oxide are known hygroscopic agents. However, calcium oxide is said to have an adverse effect on the viability of bacteria and the inclusion of silicon dioxide is said to have an adverse effect on the manufacturing process. To address these technical problems, WO 2017/060477 teaches the use of compositions containing magnesium oxide on its own as hygroscopic agent, or a special balance of 4-7% w/w magnesium oxide and 0.25-1% w/w silicon dioxide, with no further hygroscopic agent. However, it is reported in WO 2017/060477 that such inclusion of magnesium oxide leads to an unpleasant sensory experience due to its bitter taste.

Hence, there remains a need for microbial compositions which are storage stable, yet have desirable sensory properties in use, when administered orally.

The present invention seeks to provide a microbial composition which is storage stable, has good sensory properties, especially when orally administered to a subject in a powdered form.

STATEMENT OF THE INVENTION

According to a first aspect the invention provides a microbial and preferably a probiotic microbial composition in the form of a powder for oral administration comprising or consisting of:
 (i) micro-organisms;
 (ii) sugar alcohol;
 (iii) moisture absorbent fibre;
 (iv) a powder flow agent;
 optionally (v) a flavorant; and/or
 optionally (vi) a bulking agent.

In a second aspect, the invention provides a method for preparing a composition according to the first aspect of the invention comprising:
 (a) mixing ingredients (i) to (iv) and optionally (v) and/or (vi); and
 (b) packaging the mixture in a container It will be appreciated that the powdered microbial compositions of the invention are intended for direct administration to the oral cavity of a subject, that is, as a powder without prior mixing with, and/or dissolution in, a liquid such as water.

Preferably, the micro-organisms are probiotic micro-organisms. Hence, in a third aspect the invention provides a method of obtaining a probiotic effect in a subject mammal, preferably a human, comprising administering to the oral cavity of the subject an effective amount or dose of a probiotic microbial composition in the form of a powder according to the earlier aspects of the invention.

The probiotic effect may be prevention and/or reduction in the severity of one or more symptoms of a disease or disorder, especially one affecting the gastrointestinal tract of a mammal, preferably, a human.

DETAILED DESCRIPTION OF THE INVENTION

In the description of the invention various embodiments and/or individual components are disclosed. As will be apparent to the ordinarily skilled practitioner, all combinations of such embodiments and components taught in the disclosure are possible and can result in preferred embodiments of the present invention.

All percentages and ratios are calculated by weight unless otherwise indicated. All percentages, parts and ratios are calculated based on the total composition unless otherwise indicated.

Referenced herein may be trade names for components including various ingredients utilized in the present invention. However, the inventors do not intend to be limited by materials under a certain trade name. Equivalent materials (eg those obtained from a different source under a different name or reference number) to those referenced by trade name may be substituted and used in the embodiments of the invention described herein.

(i) Micro-Organisms

The micro-organisms used in the compositions of the present invention may be any viable micro-organisms, such as bacteria or fungi. Preferably, the micro-organisms are probiotic, that is, micro-organisms which, upon administration, confer a health benefit to a recipient mammal, preferably a human. The composition may comprise a single species or strain of a probiotic bacterium, or it may comprise a combination of one or more species or strains.

In one embodiment of the present invention, the micro-organism is probiotic bacteria, preferably a gram positive bacterium, preferably a Lactobacillales. In yet a further embodiment, the Lactobacillales is selected from the list consisting of a *Lactobacillus* spp., *Leuconostoc* spp., *Pediococcus* spp., *Lactococcus* spp, *Streptococcus* spp., *Aerocossus* spp., *Carnobacterium* spp., *Enterococcus* spp., *Oenococcus* spp., *Sporolactobacillus* spp., *Tetragenococcus* spp., *Vagococcus* spp., and *Weisella* spp. In a preferred embodiment, the Lactobacillales is a *Lactobacillus* spp. selected from the group consisting of *Lactobacillus rhamnosus, Lactobacillus paracasei, Lactobacillus reuteri, Lactobacillus acidophilus, Lactobacillus helveticus, Lactobacillus casei, Lactobacillus salivarius, Lactobacillus plantarum,*

*Lactobacillus fermentum, Lactobacillus johnsonii*, and *Lactobacillus gasseri*. In an even more preferred embodiment, the probiotic bacteria is a *Lactobacillus* strain selected from the group consisting of *Lactobacillus rhamnosus* GG (ATCC 53103), *Lactobacillus rhamnosus* SP1 (DSM 21690), *Lactobacillus rhamnosus* CGMCC 1.3724, *Lactobacillus reuteri* (ATCC 55730), *Lactobacillus reuteri* (DSM 17938) and *Lactobacillus johnsonii* (NCC533; CNCM 1-1225).

In one embodiment of the present invention, the probiotic bacteria is a *Lactococcus* ssp. such as a *Lactococcus* ssp. selected from the group consisting of *Lactococcus lactis, Lactococcus cremoris, Lactococcus diacetylactis*.

In another embodiment of the present invention, the probiotic bacteria is a Bifidobacteriales. In a further embodiment, the probiotic bacteria is a *Bifidobacterium* spp. such as a *Bifidobacterium* spp. selected from the group consisting of *Bifidobacterium lactis, Bifidobacterium longum, Bifidobacterium breve, Bifidobacterium infantis, Bifidobacterium animalis, Bifidobacterium bifidum* and *Bifidobacterium adolescentis*. In a preferred embodiment, the probiotic bacteria is a *Bifidobacterium* strain selected from the group consisting of *Bifidobacterium Lactis* BI-04, *Bifidobacterium lactis* CNCM 1-3446 (Bb12), *Bifidobacterium longum* NCC3001, ATCC BAA-999 (BB536), *Bifidobacterium breve* Bb-03, *Bifidobacterium breve* M-16V, *Bifidobacterium breve* R0070 and *Bifidobacterium infantis*.

In order to obtain the desired health benefit to the subject, it may be advantageous to include more than one microorganism in the composition. Thus, the composition may comprise more than one species/strain of microorganisms, such as two, three, four, five or a higher plurality of species/strains of microorganism. In one embodiment, the composition comprises at least two species of probiotic bacteria, for example at least one *Lactobacillus* spp and at least one *Bifidobacterium* spp., for example *Bifidobacterium Lactis* BI-04 and one *Lactobacillus* spp. or *Lactobacillus Rhamnosus* GG and one *Bifidobacterium* spp. In a preferred embodiment, the composition comprises *Lactobacillus Rhamnosus* GG and *Bifidobacterium Lactis* BI-04, preferably *Lactobacillus Rhamnosus* GG and *Bifidobacterium Lactis* BI-04 and no further microorganism.

Particularly preferred probiotic bacterial strains for use in the compositions of the invention may be selected from one or more of: *Lactobacillus plantarum* 299v (DSM 9843); *Lactobacillus paracasei* 8700:2 (DSM 13434) and *Lactobacillus plantarum* HEAL9 (DSM 15312); *Lactobacillus plantarum* 299 (DSM 6595); *Lactobacillus rhamnosus* 271 (DSM 6594); *Lactobacillus paracasei* 8700:2 (DSM 13434); and *Bifidobacterium bifidum* BB01.

Preferably, the probiotic bacteria used in the compositions of the invention are provided in the form of a freeze-dried powder.

The viability of the probiotic bacteria may be confirmed by plating the bacteria on a suitable medium (eg solidified agar in a standard sized Petri dish) and counting the number of colonies formed. The measure, colony forming unit (or CFU), is used to quantify the amount of viable (live) bacteria in the composition.

Thus, the initial colony forming units (CFU) and the continued stability and viability of the composition partly depend on the amount of moisture in the composition. As described herein, the composition is packaged and stored in containers (preferably sealed container) in order to provide oxygen and moisture barrier in order to protect the integrity of the probiotic bacteria in the composition.

The colony forming units (CFU) referred to in the context of the composition of the present invention are CFU in a single dose after the preparation of the composition.

Preferably, the probiotic bacteria are present in the compositions of the invention at a CFU per dose of from $10^3$-$10^{12}$ CFU/dose to $10^8$-$10^{11}$ CFU/dose.

It will be appreciated that it is the CFU of probiotic bacteria which is important, not the weight percentage amount included in the compositions. However, the probiotic bacteria are typically present in an amount from 0.4 to 10% w/w of the composition, for example, 5 to 8% w/w.

(ii) Sugar Alcohol

Sugar alcohols are substances which can be added to foods, drinks and other nutritional products to lend a sweet taste with fewer calories than sugars such as sucrose. Examples include xylitol, sorbitol, erythritol, maltitol, lactitol, isomalt, inositol and mannitol.

Preferably, the sugar alcohol (ii) is present in the compositions of the invention in an amount of from 60-80% w/w, more preferably from 67-68% w/w.

Preferably, the compositions of the invention include the sugar alcohol erythritol and/or xylitol. Most preferably, erythritol is included in combination with xylitol.

Preferably, the ratio of the amount of erythritol to xylitol is approximately 2:1, with a particularly preferred composition having 45-46% w/w erythritol and 22-23% w/w xylitol.

(iii) Moisture-Absorbent Fibre

The moisture-absorbent fibre functions to bind free water in the probiotic compositions of the invention and thereby improves the storage stability of the compositions prior to oral administration in use. This free water binding property also permits the incorporation of greater amounts of sugar alcohol into the powder formulation than would be possible without inclusion of such fibre and this contributes to the desirable fast-melt and sensory properties of the composition.

The moisture-absorbent fibre also functions to improve the consistency and mouthfeel of the probiotic composition, in use, which allows any added flavorant to stay in the mouth for the desired period of time to achieve the optimal taste and sensory experience for a recipient.

It is known to include non-digestible oligosaccharides fibres in probiotic compositions for the purpose of achieving a prebiotic effect, that is, stimulating selectively the growth and/or activity of probiotic bacteria, which can improve host health. However, it will be appreciated that in accordance with the present invention the moisture absorbent fibre is used for a non-prebiotic purpose, namely moisture absorbence to improve storage stability prior to oral administration and in use, to achieve a desirable consistency and mouthfeel, to improve the sensory experience of the recipient.

As used herein, the term "fibre" means carbohydrate polymers including those naturally occurring in food as consumed, those having been obtained from food raw material by physical, enzymatic or chemical means, and synthetic carbohydrate polymers, which are resistant to digestion and absorption in the small intestine and have partial fermentation in the large intestine.

Non-limiting examples of fibre and analogous carbohydrate polymers suitable for use in the compositions of the present invention include pectins, psyllium, guar gum, xanthan gum, alginates, gum Arabic, fructo-oligosaccharides, inulin, agar, beta-glucans, chitins, dextrins, lignin, celluloses, non-starch polysaccharides, carrageenan, and mixtures and/or combinations thereof.

In the fast-melt probiotic powder compositions of the present invention the moisture absorbent fibre be may a prebiotic fibre.

Many forms of "fibre" exhibit some level of prebiotic effect. Thus, there is considerable overlap between substances that can be classified as "prebiotics" and "fibres".

Non-limiting examples of prebiotic fibres suitable for use in the compositions of the invention as a moisture absorbent fibre include psyllium, fructo-oligosaccharides, inulin, oligofructose, galacto-oligosaccharides, isomalto-oligosaccharides xylo-oligosaccharides, soy-oligosaccharides, gluco-oligosaccharides, mannan-oligosaccharides, arabinogalactan, arabinxylan, lactosucrose, glucomannan, lactulose, polydextrose, oligo-dextran, gentioligosaccharide, pectic oligosaccharide, xanthan gum, gum Arabic, hemicellulose, resistant starch and its derivatives, and mixtures and/or combinations thereof.

Preferred examples of suitable fibres include oligosaccharides, such as inulin and its hydrolysis products commonly known as fructo-oligosaccharides, galacto-oligosaccharides, xylo-oligosaccharides, and oligo derivatives of starch.

The fibre can be provided in the form of a plant material which contains the fibre. Non-limiting examples of suitable plant materials include asparagus, artichoke, onion, wheat, chicory, beet pulp, residues of these plant materials, and mixtures thereof.

A non-limiting example of a fibre from such a plant material is inulin extract from chicory. Suitable inulin extracts can be obtained from BENEO GmbH, Maximillianstrasse 10, 68165 Mannheim (Germany)—www.beneo-.com under the trade name, Orafti® inulin.

A most preferred inulin for use as a moisture absorbent fibre in the compositions of the invention is Oraft® ST-Gel, which is provided as a powder and typically has an average degree of polymerization (DP) of ≥10 and a sweetness level approximately 10% of the sweetness of sucrose.

Alternatively, an oligo-saccharide can be obtained by hydrolyzing inulin, by enzymatic methods, or by using microorganisms as will be understood by those of skill in the art.

The compositions of the invention can comprise moisture absorbent fibre in an amount of from about 20-30% w/w, more preferably 20-25 and 22-23% w/w. Preferably the ratio of (ii) sugar alcohol to (iii) moisture absorbent fibre is approximately 3:1.

(iv) Powder Flow Agent

The powder flow agent may be any conventional powder excipient or processing aid. However, it is preferred that the flow agent is silicon dioxide, especially silicon dioxide powder available under the brand name SYLOID® 244FP from W. R Grace & Co., which has an average particle size of approximately 2.5-3.7 µm, when measured using a Malvern Mastersizer 2000; test method—Grace Q013. Alternatively, silicon dioxide powder available under the brand name SYLOID® 244 can be used. This has a particle size maximum of 8.3 µm, when measured with a Malvern Mastersizer 2000; test method—GRA1506.

Preferably, the flow agent is present in an amount of from 0.25-1% w/w, more preferably 0.5% w/w.

(v) Flavorant

The compositions of the present invention can comprise a flavorant. One or more flavorants can be incorporated in the compositions in order to enhance their palatability. Flavorants can be particularly important in compositions to be administered to children. Any natural or synthetic flavorant and/or mixtures and/or combinations thereof can be used in the present invention. Particularly suitable for use in the present invention are fruit flavors. These fruit flavors can be derived from natural sources such as fruit juices and flavour oils, or may alternatively be synthetically prepared.

A preferred flavorant is lemon flavor.

Non-limiting examples of suitable flavors are exotic and lactonic flavors including, for example, passion fruit flavors, mango flavors, pineapple flavors, cupuacu flavors, guava flavors, cocoa flavors, papaya flavors, peach flavors, and apricot flavors. In addition, a variety of other fruit flavors can be utilized, non-limiting examples of which include, apple flavors, citrus flavors, grape flavors, raspberry flavors, cranberry flavors, cherry flavors, grapefruit flavors, and the like.

Non-limiting examples of additional flavorants and mixtures and/or combinations thereof include vanilla, honey lemon, lemon honey, cherry vanilla, peach, honey ginger, cherry, cherry cream, mint, vanilla mint, dark berry, black berry, raspberry, peppermint, spearmint, honey peach, acai berry, cranberry, honey cranberry, tropical fruit, dragon fruit, wolfberry, red stem mint, pomegranate, blackcurrant, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brule, caramel, caramel nut, butter, butter toffee, caramel toffee, aloe vera, whiskey, rum, cocoa, licorice, pineapple, guava, melon, watermelon, elderberry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, and mixtures and/or combinations thereof.

The amount of flavorant used will vary, depending on the flavorants used and the character or intensity of flavour desired in the finished composition. One of ordinary skill in the art can readily make such determination. However, a preferred composition of the invention comprises approximately 1% w/w of a flavorant especially lemon flavorant.

(vi) Bulking Agent

Optionally, the compositions of the invention, may include a dry bulking agent, such as maltodextrin, to lower the water activity of the composition as a whole. For example, the bulking agent may be included in an amount of approximately 5% w/w.

Water Activity

Water activity is the ratio of the vapor pressure of water in a material (p) to the vapor pressure of pure water (po) at the same temperature. Relative humidity of air is the ratio of the vapor pressure of air to its saturation vapor pressure. When vapor and temperature equilibrium are obtained, the water activity of the sample is equal to the relative humidity of air surrounding the sample in a sealed measurement chamber. Multiplication of water activity by 100 gives the equilibrium relative humity (ERH) in percent.

$$aw=p/po=ERH\ (\%)/100$$

Water activity is a ratio of vapor pressures and thus has no units. It ranges from 0.0 aw (completely dry) to 1.0 aw (pure water).

The water activity in the composition of the invention is typically less than 0.15 and preferably less than 0.10, such as in the range of 0.05 to 0.10 water activity. The water activities referred to in the context of the compositions of the invention are the initial water activities of the composition, ie the water activity of the composition immediately after its preparation.

Water activity can be measured at 25° C. using instruments known in the art, such as the Aqualab 4TE form LABCELL LTD (www.labcell.com), Unit 3a, Mansfield Park, Four Marks, Alton, Hants, England GU34 5P.

Powdered Form

The composition is in the form of a powder. By "powder" we mean a free flowing plurality of particles.

In one embodiment, 35 to 95% of the particles have a particle size not larger than 500 micrometer (μm), for example at least 50 to 90% of the particles have a size of not larger than 250 micrometer (μm), such as at least 60 to 80% of the particles have a size not larger than 150 and preferably 125 micrometer (μm).

In one embodiment, at least 85% of the particles have a size which falls within the range of 60 to 500 and preferably 90 to 250 micrometer, for example at least 88% of the particles have a size in the range of 90 to 250 micrometer (μm).

It is also highly preferred that in the probiotic fast melt compositions of the invention, the particle size profile of the sugar alcohol(s) (e.g. erythritol and/or xylitol) and moisture absorbent fibre(s) (e.g. inulin) is as described above in this section.

The ingredients of the compositions of the invention may be mixed to homogeneity using known cone- or v-shaped blenders.

Packaging

The compositions of the present invention are typically filled in a sealed container, which provides an oxygen and moisture barrier in order to protect and maintain the viability of the probiotic bacteria in the composition.

Preferably the composition is packaged in sealed aluminium foil sticks, where each stick comprises one dose of the composition, i.e. one dose of the probiotic bacteria.

Accordingly, one aspect of the present invention concerns a container containing the composition of the present invention. Non limiting examples of suitable containers include a stick, bag, pouch or capsule. In a preferred embodiment, the container is an aluminium foil or a polyethylene stick, which is typically sealed by welding. The stick is typically configured for easy tear opening. The stick may have a tear notch.

The water activity in the composition at the time point of filling and sealing the container is preferably less than 0.15 and preferably less than 0.10, such as in the range of 0.05 to 0.01 water activity.

Methods of Administration and use to Obtain a Probiotic Effect

The compositions described herein are dosed in the form of a powder and can be packaged in a sachet, or tubular form such as a stick pack or straw. They are orally administered as a powder.

As used herein, the term "orally administering" with respect to the subject means that the mammal ingests or a human is directed to administer, or does administer, to oneself (or another human or other animal) one or more of the compositions herein. Where the human is directed to administer the composition, such direction can be that which instructs and/or informs the human that use of the composition may and/or will provide the referenced benefit, for example, alleviation of one or more symptoms associated with a disease or condition. For example, such direction may be oral direction (eg through oral instruction from, for example, a physician, pharmacist, nurse, or other health professional), radio or television media (ie advertisement), or written direction (eg through written direction from, for example, a health professional (eg scripts), sales professional or organization (eg through, for example, marketing brochures, pamphlets, written media (eg Internet, electronic mail, or other computer-related media), and/or packaging associated with the composition (eg a label present on a container holding the composition). As used herein, "written" means through words, pictures, symbols, and/or other visible descriptors. Such information need not utilize the actual words used herein, for example, "human", or "treatment", but rather use of words, pictures, symbols, and the like conveying the same or similar meaning are contemplated within the scope of this invention.

By "fast-melt" we mean that the compositions of the invention are capable of dissolving or dispersing rapidly in a recipient's oral cavity (mouth) without co-administration of a liquid. Preferably, the compositions of the invention dissolve or disperse in the oral cavity (mouth) within one minute, and more preferably within 30 seconds, or 15 seconds and most preferably less than 10 seconds after administration without co-administration of a fluid.

Administration may be on an as-needed or as-desired basis, for example, once-monthly, once-weekly, or daily, including multiple times daily, to arrive at a total daily dose or amount of probiotic bacteria, whether administered every day, one day per week, one day per month, or on a given day as needed. The amount of composition utilized may be dependent on a variety of factors, including the health status of the subject mammal, age, gender, or other like factors of ordinary consideration.

In one embodiment the subject is a human child between the ages of 2 and 18, alternatively between the ages of 3 and 12 and alternatively between the ages of 6 and 9 years of age.

In another embodiment, the subject is a woman of childbearing age, or a post-menopausal woman, or an adult male human.

BRIEF DESCRIPTION OF THE FIGURES

We describe below non-limiting examples which embody one or more aspects of the invention. These examples are described with reference to the following figures in which.

Figures 1A, 1B:
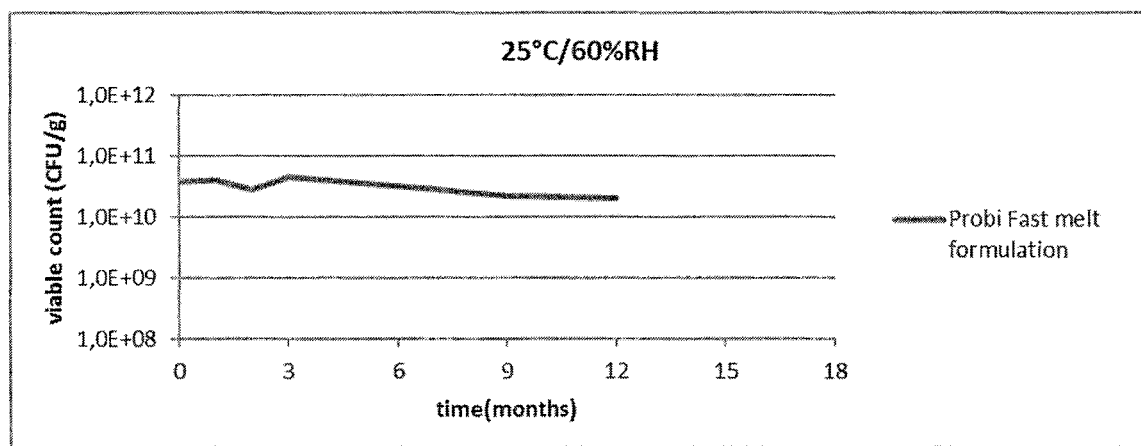
FIG. 1(a): shows the storage stability over time (months) at 25° C. and 60% relative humidity (RH) of a preferred composition of the invention ("particularly preferred composition 1") produced on a lab scale with *Lactobacillus plantarum* 299v.
FIG. 1(b): shows the water activity measurements for the composition of FIG. 1(a) over time (months).
Figures 1C, 1D:
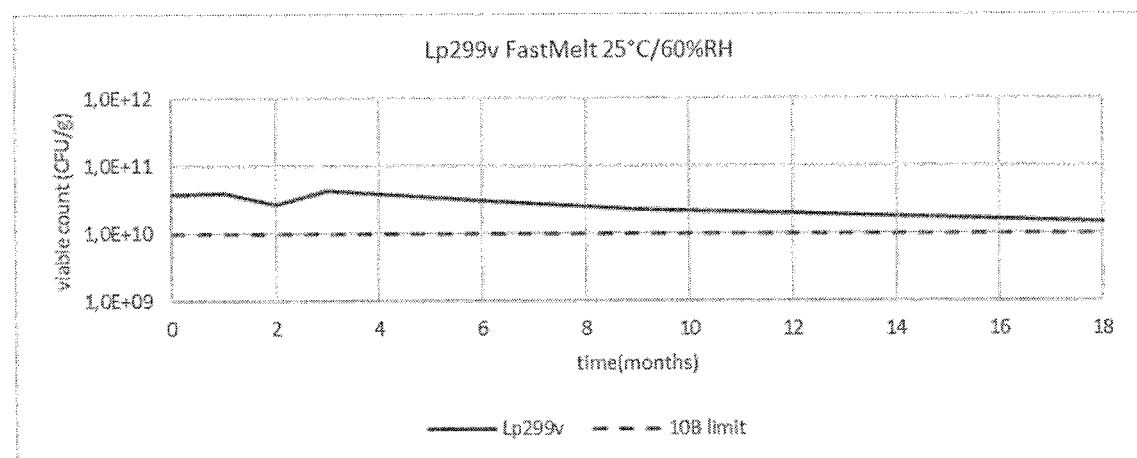
FIG. 1(c): shows the storage stability over time (months) at 25° C. and 60% relative humidity (RH) of the composition of FIG. 1(a) up to 18 months.
FIG. 1(d): shows the water activity measurements for the composition of FIG. 1(a) over time (months) up to 18 months.

In each of the figures, "10B limit" and "1B limit" represent a lower limit of 10 billion and 1 billion CFU respectively, being a desired dose for probiotic effectiveness of the particular strain(s) used in the respective figure. It will be appreciated that the storage stability of the fast melt formulations exemplified herein is such that the viable count of probiotic bacteria in each figure does not fall below the desired dose for the particular strain(s) in each of the exemplary products.

EXAMPLES

Materials and Methods

Many different types of ingredients were evaluated in order to produce a fast-melt powder formulation probiotic bacteria with a low water activity (<0.15) and desired sensory properties.

The water activities of the different ingredients were measured at 25° C. with the instrument Aqualab 4TE. When the water activity values of any ingredient were higher than 0.15, drying of the ingredients was performed on a lab scale by adding desiccant bags together with the powder in sealed aluminium bags for 1-3 days. After the drying step the water activity was measured again.

The sensory properties of the ingredients were evaluated regarding to consistency, mouthfeel, particle size, melting properties in mouth, taste and sweetness. The sensory evaluation was performed by a panel of qualified personnel.

Addition of a moisture absorbent fibre (inulin) was able to achieve a lower total water activity and also a preferred mouthfeel property.

Further, a dry bulking agent, such as maltodextrin, could be added to the formulation in order to lower its total water activity.

A probiotic strain or combination of strains was added to give the preferred probiotic health effects. *Lactobacillus plantarum* 299v were chosen for this formulation, but other probiotic bacteria in the suggested range of $10^3$-$10^{12}$ CFU/dose and more preferred $10^8$-$10^{11}$ CFU/dose should be included.

A silicon dioxide flow agent was able to achieve a satisfactory flow of the powder during process and packaging, but other known alternative powder processing aids and powder flow agents would work as well (for example due to regulatory issues on different markets).

Flavorant(s) were added to the formulation in order to give the product a pleasant taste.

Storage stability at 25° C./60% Relative Humidity was evaluated to examine the shelf life of a preferred product over time (months).

Our next step was to industrialize the large scale production of the probiotic composition. The water activity of the ingredients of the composition was measured. If the water activity value of an ingredient was higher than 0.15, drying of the ingredient was conducted by fluidized bed drying.

Blending of the ingredients were performed using a conventional cone- or v-shaped blenders to achieve a homogenous blend with a minimized loss of the probiotic bacteria.

The final homogenous powder blend was filled in in stick packs. Handling, blending and filling of probiotic formulations are performed in a controlled atmosphere, temperature and relative humidity. The stick packs could be of different materials, but to achieve a good storage stability of the probiotic bacteria they preferably include a barrier of aluminium, to protect the powder from moisture.

Results

Evaluation of Ingredients

The evaluation of ingredients showed that the sugar alcohols were the most influential ingredient for desirable sensory properties. Erythritol has functional benefits such as a clean and natural sweet taste and it gives the desired cool mouthfeel and it melts quickly in mouth. Besides that, it has nutritional benefits such as high digestive tolerance (compared to other polyols) and is non-cariogenic. Also, Xylitol has a sugar pleasant sweet taste and a cooling mouthfeel.

Different qualities of the sugar alcohols were evaluated and the most obvious differences for the sensory experience between the qualities related to the particle size. Qualities with smaller particle sizes melted faster in the mouth and gave a more pleasant mouthfeel than the ones with larger particle sizes. It is also of importance to choose ingredients in the similar range of particle sizes, in order to more easily achieve a homogenous blend in the final composition.

Table 1, Appendix 1 shows evaluation of ingredients and the results of lab scale drying tests, particle sizes and comments from the sensory testing panel.

Formulation of Preferred Probiotic Compositions

Different combinations of ingredients were evaluated with respect to sensory properties and water activity, see table 2. After finding the desired properties a second evaluation was made to provide the most preferred formulation with specific amounts of the ingredients, see table 3.

In earlier studies using formulations with inulin and probiotic bacteria, we found that storage stability was improved considerably by the inclusion of inulin fibres. We reasoned that the fibres were binding free water in the compositions and at higher temperatures the fibres released the water. This led to decreased storage stability, that is, the count of viable bacteria fell at higher temperatures.

With reference to Table 1 it can be seen that, even after drying, the water activity of the preferred sugar alcohol erythritol was higher (0.24) than would normally be acceptable (less than 0.15). However, in light of our earlier studies we reasoned that inclusion of a moisture absorbent fibre such as inulin, could compensate for the higher than desired water activity of the sugar alcohol.

Figures 2A, 2B:
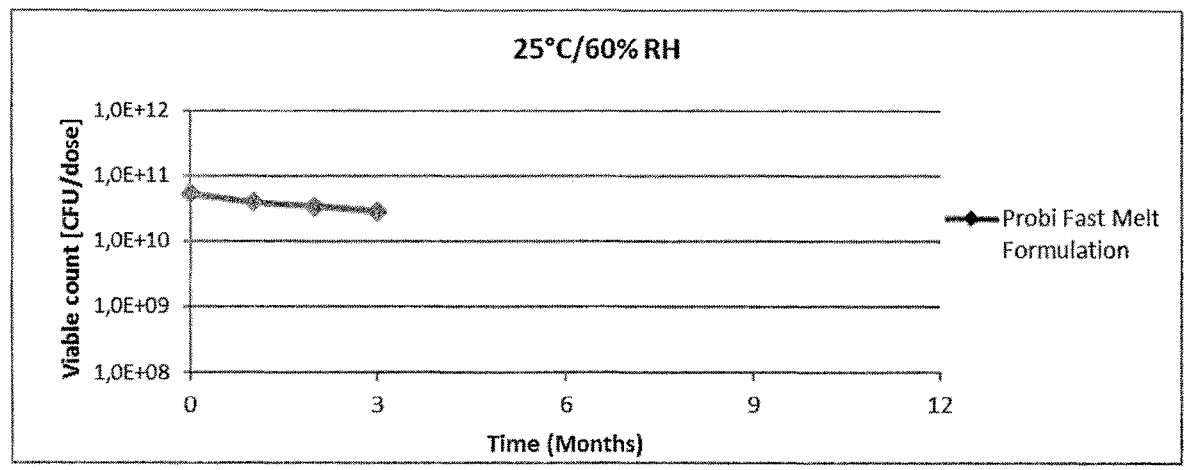
FIG. 2(a): shows the storage stability over time (months) at 25° C. and 60% relative humidity (RH) for a preferred composition of the invention ("particularly preferred composition 1") produced on an industrial scale with *Lactobacillus plantarum* 299v.
FIG. 2(b): shows the water activity measurements over time (months) for the composition of FIG. 2(a).
Figures 3A, 3B:
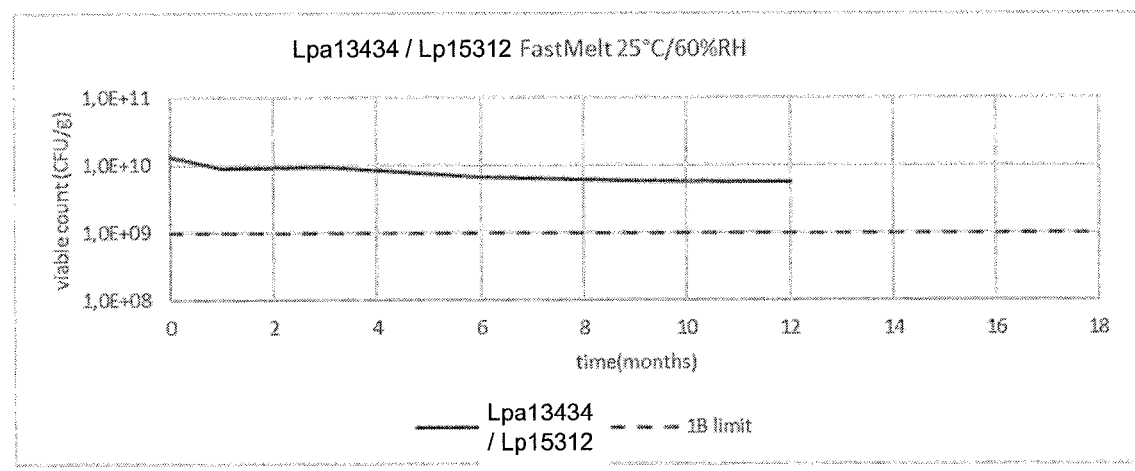
FIG. 3(a): shows the storage stability over time (months) at 25° C. and 60% relative humidity (RH) of a preferred composition of the invention described as "particularly preferred composition 1" except using a combination of *Lactobacillus paracasei* 8700:2 (DSM 13434) and *Lactobacillus plantarum* HEAL9 (DSM 15312) in place of *Lactobacillus plantarum* 299v.
FIG. 3(b): shows the water activity measurements for the composition of FIG. 3(a) over time (months).
Figures 4A, 4B:
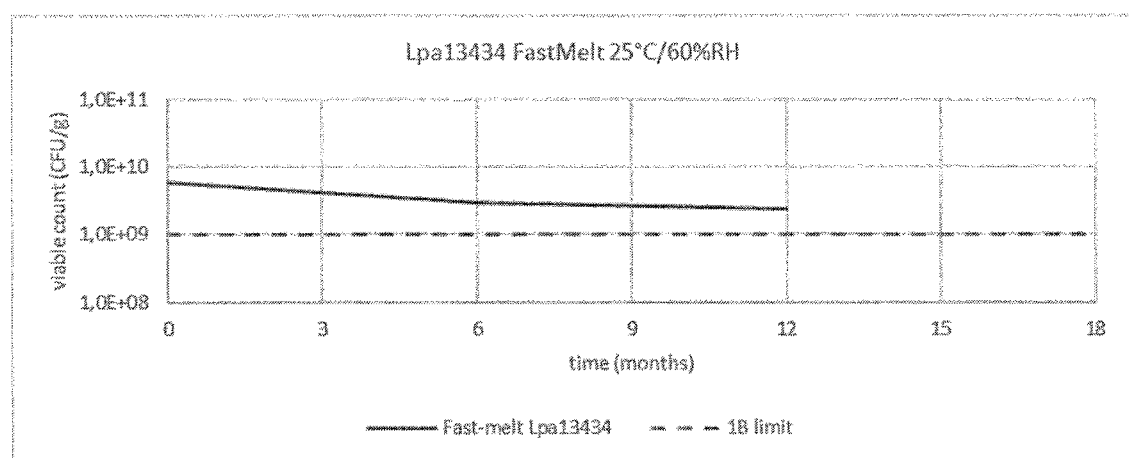
FIG. 4(a): shows the storage stability over time (months) at 25° C. and 60% relative humidity (RH) of a preferred composition of the invention described as "particularly preferred composition 1" except using *Lactobacillus paracasei* 8700:2 (DSM 13434) in place of *Lactobacillus plantarum* 299v.
FIG. 4(b): shows the water activity measurements for the composition of FIG. 4(a) over time (months).
Figures 5A, 5B:
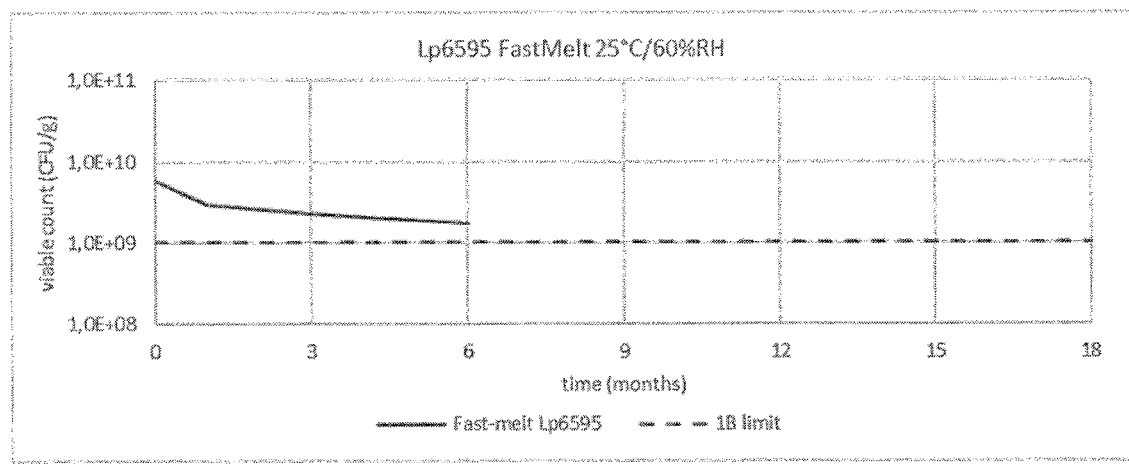
FIG. 5(a): shows the storage stability over time (months) at 25° C. and 60% relative humidity (RH) of a preferred composition of the invention described as "particularly preferred composition 1" except using *Lactobacillus plantarum* 299 (DSM 6595) in place of *Lactobacillus plantarum* 299v.
FIG. 5(b): shows the water activity measurements for the composition of FIG. 5(a) over time (months).
Figures 6A, 6B:
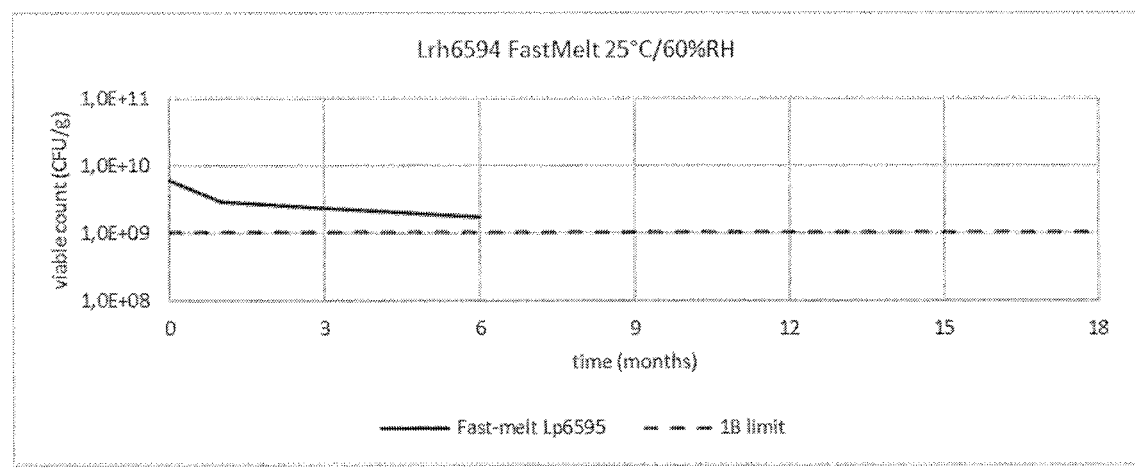
FIG. 6(a): shows the storage stability over time (months) at 25° C. and 60% relative humidity (RH) of a preferred composition of the invention described as "particularly preferred composition 1" except using *Lactobacillus rhamnosus* 271 (DSM 6594) in place of *Lactobacillus plantarum* 299v.
FIG. 6(b): shows the water activity measurements for the composition of FIG. 6(a) over time (months).

FIGS. 1(a) and 2(a) confirm that the probiotic fast melt compositions of the invention have unexpectedly good storage stability as well as desirable sensory properties.

By combining sugar alcohols, which have too high water activity on their own and which were difficult to dry to the full extent, with a moisture absorbent fibre and drying the blend, a fast-melt probiotic powder a formulation with unexpected good stability and improvement of mouthfeel was obtained.

The moisture absorbent fibre functions in two ways. It helps to bind up free water in the formulation so that the probiotic bacteria are protected from moisture even though the water activity is somewhat higher than one would normally desire due to the inclusion of sugar alcohols. This is shown with good trends of the storage stability testing of the formulation.

The other benefit of including the moisture absorbent fibre together with the sugar alcohol is that it gives the formulation the right consistency and mouthfeel, which makes the flavorant stay in mouth the desired time for the best taste experience.

A particularly preferred composition 1 of the invention with excellent storage stability and sensory properties consists of:

| Ingredient | Weight percent % w/w | Content (mg/stick pack) |
|---|---|---|
| Erythritol (sugar alcohol) | 45 | 450 |
| Inulin (moisture absorbent fibre) | 22.75 | 227.5 |
| Xylitol (sugar alcohol) | 22.75 | 227.5 |
| *Lactobacillus plantarum* 299v (probiotic bacteria) | 8 | 80 |

| Ingredient | Weight percent % w/w | Content (mg/stick pack) |
|---|---|---|
| Lemon flavour | 1 | 10 |
| Silicon dioxide (powder flow agent) | 0.5 | 5 |
| Total weight | 100 | 1000 |

Another particularly preferred composition 2 of the invention with excellent storage stability and sensory properties consists of:

| Ingredient | Weight percent % w/w | Content (mg/stick pack) |
|---|---|---|
| Erythritol | 42.5 | 425 |
| Inulin | 21.5 | 215 |
| Xylitol | 21.5 | 215 |
| Maltodextrin (dry bulking agent) | 5 | 50 |
| *L. plantarum* 299v | 8 | 80 |
| Lemon flavour | 1 | 10 |
| Silicon dioxide | 0.5 | 5 |
| Total weight | 100 | 1000 |

In FIGS. 3-6, when changing the identity of the probiotic strain in the recipe of "particularly preferred composition 1", the combined mass of erythritol, inulin and xylitol was adjusted according to the mass of powder of the replacement probiotic strain(s) without altering the internal proportion between the erythritol, inulin and xylitol.

FIGS. 3-6 confirm that the probiotic fast melt compositions of the invention have unexpectedly good storage stability as well as desirable sensory properties with several different probiotic strains. Hence, the fast melt properties of the probiotic fast melt compositions of the invention are not expected to differ according to the identity of the probiotic strain therein.

In accordance with the most preferred embodiment of the invention, in the probiotic fast melt compositions of the invention, including "particularly preferred composition 1" and "particularly preferred composition 2", the particle size profile of the sugar alcohol(s) (e.g. erythritol and/or xylitol) and moisture absorbent fibre(s) (e.g. inulin) is as described above in the section entitled "Powdered form".

TABLE 1

Evaluation of ingredients

| Ingredient | Water activity (Aw) before drying | Water activity (Aw) after drying 1-3 days | Particle size | Sensory evaluation |
|---|---|---|---|---|
| Erythritol 1 | 0.25 | 0.24 | <250 μm Max 20% | Mouthfeel like granulated sugar. Too large particles. |
| Erythritol 2 | 0.37 | 0.24 | >150 μm Max 5% >250 μm Max 0.5% | Nice mouthfeel and sweet taste. Melts quickly in mouth. Cooling effect. |
| Xylitol 1 | 0.29 | 0.11 | <100 μm Max 6% >500 μm Max 5% | Nice taste, a bit sugary. Melts quickly in mouth. Some cooling effect. |
| Xylitol 2 | | | >800 μm Max 5% <200 μm Max 10% | Too large particles. |

TABLE 1-continued

Evaluation of ingredients

| Ingredient | Water activity (Aw) before drying | Water activity (Aw) after drying 1-3 days | Particle size | Sensory evaluation |
|---|---|---|---|---|
| Sorbitol 1 | 0.27 | 0.07 | <100 μm Max 6%<br>>200 μm Min 50%<br>Max 75%<br>>500 μm Max 2% | Nice taste, a bit sugary. Melts quickly in mouth. No cooling effect. |
| Isomalt 1 | 0.29 | 0.04 | >500 μm Max 5%<br>>250 μm 20-70%<br><63 μm Max 15% | Nice taste. Disappears very quickly in mouth. Not so sweet. No cooling effect. |
| Isomalt 2 | 0.27 | 0.12 | >500 μm Max 5%<br>>250 μm 20-70%<br><63 μm Max 15% | Nice neutral taste. Disappears very quickly in mouth. Not so sweet. No cooling effect. |
| Inulin 1 | 0.16 | 0.04 | <25 μm Max 10%<br>>100 μm Min 20% | No fast melt mouth feeling. Becomes like a sugary lump directly into mouth. |
| Inulin 2 | 0.17 | 0.08 | <60 μm Max 20%<br>>150 μm Min 20% | No fast melt mouth feeling. Becomes like a sugary lump directly into mouth. |
| Oligofructose 1 | 0.20 | 0.07 | <50 μm Max 10%<br>>165 μm Min 20% | No fast melt mouth feeling. Becomes like a sugary lump directly into mouth. Sweeter taste than inulin. |

TABLE 2

Formulation Evaluation 1

| Formulation number | Bulk formulation | % | Sensory evaluation | Water activity |
|---|---|---|---|---|
| 1 | Erythritol 2<br>Isomalt 1 | 70<br>30 | Like Erythritol in both appearance and taste. With lumps. Cannot be poured. | N/A |
| 2 | Erythritol 2<br>Silicon dioxide | 99<br>1 | No lumps and easier to pour. Same taste as only Erythritol. | N/A |
| 3 | Erythritol 2<br>Silicon dioxide<br>Isomalt 1 | 69<br>1<br>30 | Free flowing. Melts quickly in mouth. Cooling effect. More balanced sweetness than for only Erythritol | 0.13 |
| 4 | Erythritol 2<br>Silicon dioxide<br>Oligofructose 1 | 69<br>1<br>30 | Relatively free flowing powder. First a cooling effect and it disappears quickly. Then a few particles left in mouth, that disappears quickly. | 0.11 |
| 5 | Erythritol 2<br>Silicon dioxide<br>Isomalt 1 | 29<br>1<br>70 | Free flowing powder. Melts a bit slower than no 3 and 4, but still rather quickly. Not so cooling effect. | 0.06 |
| 6 | Erythritol 2<br>Silicon dioxide<br>Inulin 1 | 29<br>1<br>70 | Relatively free flowing powder. Clear inulin flavor. It forms clumps in the mouth, but not that much as for only inulin. No cooling effect. | 0.04 |
| 7 | Erythritol 2<br>Silicon dioxide<br>Inulin 2<br>Xylitol 1 | 49<br>1<br>25<br>25 | Relatively free flowing powder. The particle size of xylitol is perceived a bit larger than for the other ingredients. Very nice mouthfeel. Is perceived very sweet. Melts nice in mouth, but remains for a short while. The best formulation. | 0.08 |
| 8 | Erythritol 2<br>Silicon dioxide<br>Inulin 2<br>Xylitol 1 | 49<br>1<br>35<br>15 | Stays in mouth a bit longer than formulation no 7. Clearer sweet aftertaste of the inulin. A bit less cooling effect than no. 7. Certain graininess. | 0.06 |
| 9 | Erythritol 2<br>Silicon dioxide<br>Inulin 2<br>Xylitol 1 | 49<br>1<br>15<br>35 | Free flowing powder. More cooling effect and melts faster in mouth than no. 8. Certain graininess. | 0.08 |

TABLE 3

Formulation Evaluation 2

| Formulation numb | Bulk formulation | % | Sensory evaluation | Water activity |
|---|---|---|---|---|
| 10 | Erythritol 2<br>Silicon Dioxide<br>Xylitol 1 | 59<br>1<br>40 | Disappears quickly in mouth, the mouthfeel gets a bit flat. | 0.18 |
| 11 | Erythritol 2<br>Silicon Dioxide<br>Inulin 2 | 69<br>1<br>30 | Nice mouthfeel and taste. | |
| 12 | Erythritol 2<br>Silicon Dioxide<br>Inulin 2<br>Xylitol 1 | 49<br>1<br>25<br>25 | Nice cooling effect. Melts quick in mouth but still with a certain body that gives a nice overall mouthfeel. The best formulation. | |

TABLE 3-continued

Formulation Evaluation 2

| Formulation numb | Bulk formulation | % | Sensory evaluation | Water activity |
|---|---|---|---|---|
| 13 | Erythritol 2 | 49 | Too much taste of inulin. | |
| | Silicon Dioxide | 1 | | |
| | Inulin 2 | 35 | | |
| | Xylitol 1 | 15 | | |
| 14 | Erythritol 2 | 49 | Too sweet taste. | |
| | Silicon Dioxide | 1 | Disappears quickly in | |
| | Inulin 2 | 15 | mouth. | |
| | Xylitol 1 | 35 | | |
| 15 | Erythritol 2 | 39 | Not that cooling effect. | |
| | Silicon Dioxide | 1 | Clear inulin taste | |
| | Inulin 2 | 30 | | |
| | Xylitol 1 | 30 | | |

TABLE 4

Weight % and particle sizes for preferred composition

| Ingredient | Weight percentage | Max 8.3 | <60 | 63 | >90 | <100 | >125 | >150 | >250 | >500 | >710 | μm |
|---|---|---|---|---|---|---|---|---|---|---|---|---|
| Erythritol 2 | 45% | | | | | | | max 5% | max 0.5% | | | |
| Xylitol 1 | 22.75% | | | | | max 6% | | | | max 5% | | |
| Inulin 2 | 22.75% | | max 20% | | | | | Min 20% | | | | |
| Silicon dioxide | 0.50% | 100% | | | | | | | | | | |
| Lp299v | 8% | | | | 10% | 5% | | 30% | 40% | 15% | 3% | |

The invention claimed is:

1. A microbial composition in the form of a powder for oral administration, comprising or consisting of:
   (i) micro-organisms;
   (ii) sugar alcohol;
   (iii) a moisture absorbent fibre;
   (iv) a powder flow agent;
   optionally (v) a flavorant;
   optionally (vi) a bulking agent;
   wherein:
   a) the moisture absorbent fibre is inulin, and is in an amount from 20-25% w/w,
   b) the microbial composition has a water activity of less than 0.15,
   c) the ratio of (ii) sugar alcohol to (iii) moisture absorbent fibre is 3:1, and
   d) the sugar alcohol is erythritol, or the sugar alcohol is a combination of erythritol and xylitol in a ratio of 2:1.

2. A microbial composition as claimed in claim 1 wherein the powder flow agent is silicon dioxide.

3. A microbial composition as claimed in claim 1 wherein the bulking agent is maltodextrin.

4. A microbial composition as claimed in claim 1 wherein the micro-organisms are probiotic bacteria.

5. A microbial composition as claimed in claim 4, wherein the probiotic bacteria are selected from *Lactobacillus* spp. and/or *Bifidobacterium* spp.

6. A microbial composition as claimed in claim 1 wherein the micro-organisms are present in an amount of from $10^3$-$10^{12}$ colony forming units (CFU)/dose.

7. A microbial composition as claimed in claim 6, wherein the micro-organisms are present in an amount of from $10^8$-$10^{11}$ colony forming units (CFU)/dose.

8. A sealed container filled with one or more doses of a microbial composition as claimed in claim 1.

9. A sealed container as claimed in claim 8 in the form of a sachet or in tubular form.

10. A sealed container as claimed in claim 9, wherein the tubular form is a stick pack or straw.

11. A method of making a packaged microbial composition as claimed in claim 1 comprising
   (a) mixing ingredients (i)-(iv) and optionally (v) and/or (vi); and
   (b) packaging the mixture in a sealed container.

12. A method as claimed in claim 11 wherein one or more of the ingredients is dried to a water activity of less than 0.15 prior to mixing step (a).

* * * * *